(12) United States Patent
Katscher et al.

(10) Patent No.: US 7,839,147 B2
(45) Date of Patent: Nov. 23, 2010

(54) SHIMMING OF ELECTRIC FIELD FOR ELECTRIC PROPERTIES TOMOGRAPHY

(75) Inventors: Ulrich Katscher, Norderstedt (DE);
Peter Vernickel, Hamburg (DE); Marius Hanft, Saarbruecken (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 87 days.

(21) Appl. No.: 12/297,662

(22) PCT Filed: Nov. 8, 2007

(86) PCT No.: PCT/US2007/065850

§ 371 (c)(1),
(2), (4) Date: Oct. 20, 2008

(87) PCT Pub. No.: WO2007/127581

PCT Pub. Date: Nov. 8, 2007

(65) Prior Publication Data

US 2009/0102480 A1    Apr. 23, 2009

(51) Int. Cl.
*G01V 3/00* (2006.01)
(52) U.S. Cl. .................. 324/318; 324/309
(58) Field of Classification Search ......... 324/300–322; 600/407–445
See application file for complete search history.

(56) References Cited

U.S. PATENT DOCUMENTS

| | | | |
|---|---|---|---|
| 5,284,142 A | | 2/1994 | Goble et al. |
| 5,731,704 A | * | 3/1998 | Schnur et al. ............. 324/320 |
| 5,839,437 A | * | 11/1998 | Briggs, III ............. 128/207.17 |
| 5,897,495 A | * | 4/1999 | Aida et al. ................. 600/411 |
| 6,192,262 B1 | * | 2/2001 | Godik ........................ 600/407 |
| 6,397,095 B1 | | 5/2002 | Eyuboglu et al. |
| 7,048,716 B1 | * | 5/2006 | Kucharczyk et al. ... 604/164.01 |

(Continued)

FOREIGN PATENT DOCUMENTS

GB     2056088 A     3/1981

(Continued)

OTHER PUBLICATIONS

Collins, C. M., et al.; Different Excitation and Receoption Distributions with a Single-Loop Transmit-Receive Surface Coil Near a Head-Sized Spherical Phantom at 300 MHz; 2002; MRM; 47:1026-1028.

(Continued)

*Primary Examiner*—Brij B Shrivastav

(57) ABSTRACT

A radio frequency coil system (34) used in the context of electric properties tomography (EPT, electrical impedance tomography, EIT, applied potential tomography, APT) generates radio frequency excitation pulses in an examination region (14). The radio frequency coil system (34) includes N coil elements (38) which generate magnetic (H) and electric (E) fields. A weight setting device (54) sets weight factors for input signals for the coil elements (38). A transmitting system (52) creates RF pulses, at least two sets of each with differently weighted input signals, and transmits the at least two sets of RF pulses to the coil elements (38) such that each of the transmitted RF pulse sets generates shifted electric fields (110, 112) having a shifted zero crossing point (120, 122) from each other. An image processor (62) computes electric permittivity maps from resonance induced by the at least two sets of RF pulses with different weighting.

19 Claims, 3 Drawing Sheets

U.S. PATENT DOCUMENTS

| | | | |
|---|---|---|---|
| 7,082,325 | B2 * | 7/2006 | Hashimshony et al. ....... 600/411 |
| 2005/0054911 | A1 | 3/2005 | Nachman et al. |
| 2007/0258329 | A1 * | 11/2007 | Winey ........................ 367/140 |
| 2007/0293753 | A1 * | 12/2007 | El-Sharkawy et al. ....... 600/412 |

FOREIGN PATENT DOCUMENTS

| | | |
|---|---|---|
| WO | 2004026136 A1 | 4/2004 |
| WO | 2007017779 A2 | 2/2007 |

OTHER PUBLICATIONS

Haacke, E. M., et al.; Extraction of conductivity and permittivity using magnetic resonance imaging; 1991; Phys. Med. Biol.; 36(6)723-734.

Kiruluta, A. J. M.; Field propagation phenomena in ultra high field NMR: A Maxwell-Bloch formulation; 2006; Journal of Magnetic Resonance; 182(2)308-314.

Mihara, H., et al.; Imaging of the dielectric resonance effect in high field magnetic resonance imaging; 2005; Journal of Applied Physics; 97(10)10R305.

Huang, et al., "Outline of the Reconstruction Method for MR-NT", Proc. Intl. Soc. Mag. Reson. Med. 13 (2005).

Gençer, et al., "Electrical Impedance Tomography: Induced-Current Imaging Achieved with a Multiple Coil System", IEEE Trans. on Biomedical Engineering, vol. 45, No. 2, Feb. 1996.

Joines, et al., "The Measured Electrical Properties of Normal and Malignant Human Tissues From 50 to 900 MHz", Med. Phys. 21 (4) Apr. 1994 p. 547-550.

Saulnier, et al. "Electrical Impedance Tomography", IEEE Signal Processing Magazine, Nov. 2001, p. 31-43.

* cited by examiner

SHIMMING OF ELECTRIC FIELD FOR ELECTRIC PROPERTIES TOMOGRAPHY

The present application relates to the magnetic resonance arts. It finds particular application in electric properties tomography (EPT) and will be described with particular reference thereto. More generally, it finds application in magnetic resonance systems for imaging, spectroscopy, and so forth.

Magnetic resonance imaging (MRI) scanners typically include a main magnet, typically superconducting, which generates a spatially and temporally constant magnetic field $B_o$ through an examination region. A radio frequency (RF) coil, such as a whole-body coil, a head coil, and the like, and a transmitter are tuned to the resonance frequency of the dipoles to be imaged in the $B_o$ field. The coil and transmitter are used to excite and manipulate the dipoles. Spatial information is encoded by driving the gradient coils with currents to create magnetic field gradients in addition to the $B_o$, field across the examination region in various directions. Magnetic resonance signals are acquired by the same or separate receive-only RF coil, demodulated, filtered and sampled by an RF receiver and finally reconstructed into an image on some dedicated or general-purpose hardware.

Recently, the magnetic resonance systems have been used to derive electromagnetic properties, such as electric conductivity and permittivity, of the imaged subject. The electric conductivity and permittivity of the subject are viable characteristics for discriminating between different tissues as the different biological tissues appear to have different values of the electrical permittivity. For example, the electric properties tomography method is useful in distinguishing between tumors and healthy tissue, as the tumors typically have elevated values of both electric conductivity and permittivity. The electric properties tomography method is also useful in distinguishing cerebral edema, necrotic tissue after a myocardial infarction, and other pathologies as the pathological tissue exhibits a dielectric contrast to the surrounding tissue.

In an electric properties tomography (EPT) system, electric conductivity and permittivity distribution in the imaged subject are derived from the magnetic induction field strength distribution obtained from the magnetic resonance signals. As the magnetic resonance system is known to have an exceptional spatial resolution, the conductivity and permittivity distribution in the patient too can be derived with exceptional spatial resolution.

However, the values of the electrical permittivity cannot be accurately derived for the entire field of view. Typically, the radio frequency coils exhibit one or more null points zero crossings of the electric field in the field of view. As the electric permittivity is inversely proportional to the z-component of the electric field, the electric permittivity can be accurately computed only for the regions where the values of the electric field are significantly greater than zero. Thus, imaging of complete slices is hampered.

The present application provides new and improved methods and apparatuses which overcome the above-referenced problems and others.

In accordance with one aspect, a magnetic resonance imaging apparatus is disclosed. A radio frequency coil system generates radio frequency excitation pulses in an examination region, radio frequency coil system including N coil elements which generate magnetic and electric fields, where N is a plural number. A weight setting device sets weight factors for input signals for the coil elements. A transmitting system creates RF pulses, at least two sets of each with differently weighted input signals, and transmits the at least two sets of RF pulses to the coil elements such that each of the transmitted RF pulse sets generates shifted electric fields having a shifted zero crossing point from each other. An image reconstruction processor computes electric permittivity maps from resonance induced by the at least two sets of RF pulses with different weighting.

In accordance with another aspect, a method for determining at least one electromagnetic property of a subject is disclosed. The method comprises (a) setting a weight factor for an input signal for each individual radio frequency coil element; (b) transmitting RF pulses with the set weight factors to corresponding coil elements to generate a set of resonance data; (c) repeating steps (a) and (b) with different weighting factors to shift a zero electric field crossing point; and (d) reconstructing an electric permittivity map from the shifted electric fields.

In accordance with another aspect, a system for deriving electromagnetic properties of an imaged subject is disclosed. A main magnet generates a main magnetic field through an examination region. A plurality of RF coil elements is disposed adjacent the examination region for generating magnetic and electric fields. A weight setting device sets weight factors for input signals for the coil elements. A transmitting system creates RF pulses in accordance with the determined input signals and transmits the RF pulses to corresponding coil elements such that the transmitted RF pulses generate at least shifted electric fields in each corresponding coil element, a z-component value of each generated electric field having a shifted zero crossing point. An electric permittivity map computing processor superpositions the shifted electric fields to receive non-zero z-component values of a total electric field and computes electric permittivity distribution in the imaged subject from the superpositioned data. A reconstruction processor reconstructs a volumetric data representation of an entire field of view from the computed electric permittivity distribution.

One advantage is that the permittivity distribution can be accurately derived for the entire field of view.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
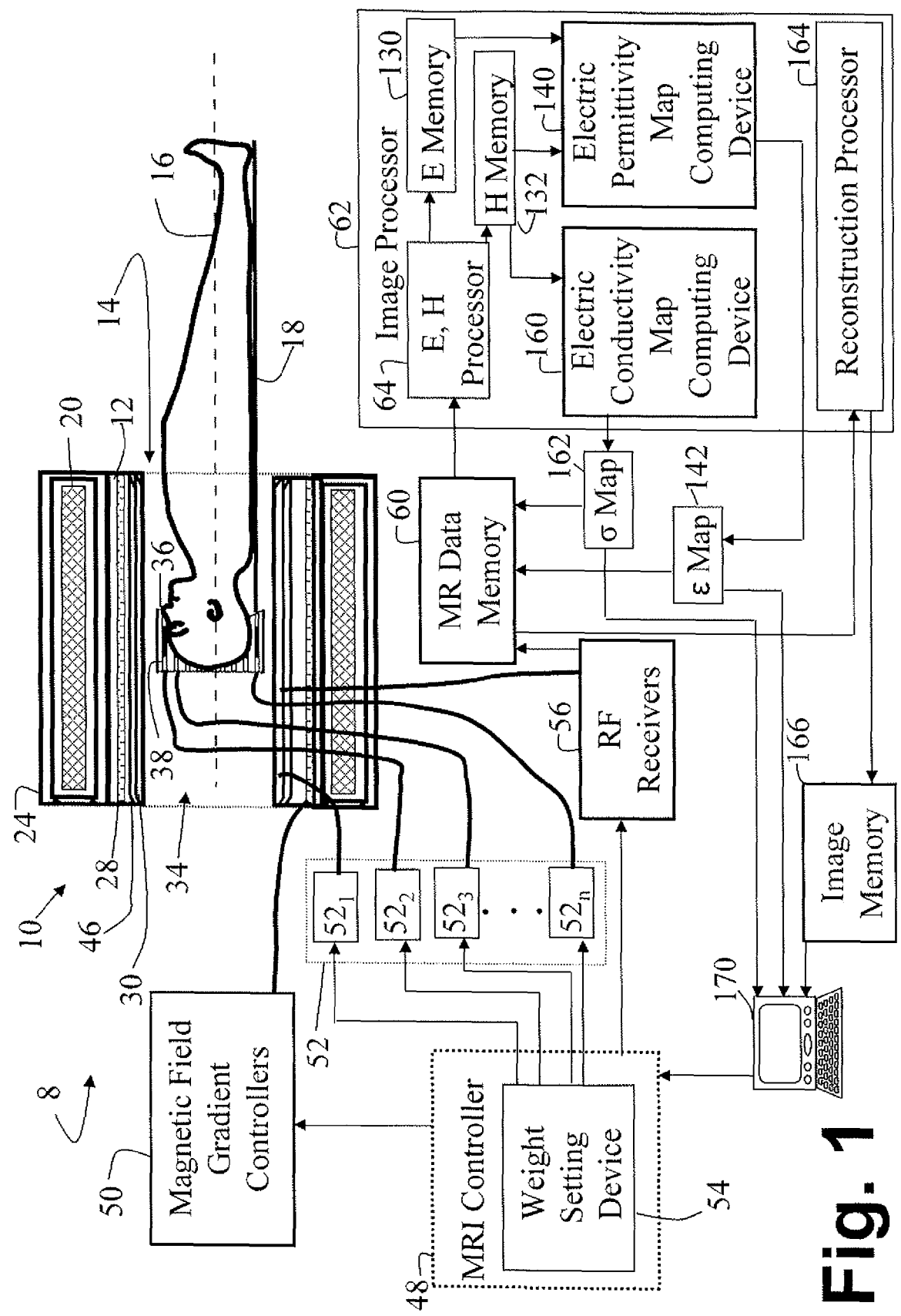
FIG. 1 is a diagrammatic illustration of a magnetic resonance imaging system.

With reference to FIG. 1, a magnetic resonance imaging system 8 includes a scanner 10 including a housing 12 defining an examination region 14, in which is disposed a patient or other imaging subject 16 on a patient support or bed 18. A main magnet 20 disposed in the housing 12 generates a main magnetic field in the examination region 14. Typically, the main magnet 20 is a superconducting magnet surrounded by cryo shrouding 24; however, a resistive or permanent main magnet can also be used. Magnetic field gradient coils 28 are arranged in or on the housing 12 to superimpose selected magnetic field gradients on the main magnetic field within the examination region 14.

A whole-body radio frequency coil 30, such as a TEM coil, SENSE coil elements, a birdcage coil, a hybrid TEM-birdcage coil, an arrangement of resonators, or the like, is arranged in the housing 12 to inject radio frequency excitation pulses into the examination region 14 and to detect generated magnetic resonance signals. For generating images of limited regions of the subject 16, an RF coil system or arrangement 34 which includes one or more radio frequency coils 36 can be disposed about the examination region 14. The coil 36 includes a plurality of radio frequency coil elements, segments, resonators, or rungs 38 which each might have a different size and position. The coil 36 may be a TEM coil, a hybrid TEM-birdcage coil, a birdcage resonator, an arrangement of resonators, or the like. In the exemplary embodiment, the coil 36 includes a plurality of resonators 38 positioned around or in the intended volume of examination. The coil 36 is, for example, circularly cylindrical, but, of course, might have other geometries, such as an elliptic cross-section, semi-circular cross-section, semi-elliptical cross-section, and the like. An RF shield 46 shields the coils 30, 36 from the surrounding elements.

The described magnetic resonance imaging system 8 is an illustrative example. In general, substantially any magnetic resonance imaging scanner can incorporate the disclosed radio frequency coils. For example, the scanner 10 can be an open magnet scanner, a vertical bore scanner, a low-field scanner, a high-field scanner, or so forth.

With continuing reference to FIG. 1, a magnetic resonance imaging controller 48 operates magnetic field gradient controllers 50 coupled to the gradient coils 28 to superimpose selected magnetic field gradients on the main magnetic field in the examination region 14, and also operates a radio frequency transmitting system 52 which includes transmitting channels or transmitters $52_1, 52_2, \ldots, 52_n$, each coupled to one or more radio frequency coil segments 38 to inject selected radio frequency excitation pulses at about the magnetic resonance frequency into the examination region 14 for imaging. The radio frequency transmitters $52_1, 52_2, \ldots, 52_n$ are individually controlled and can have different phases and amplitudes. For example, a weight determining processor, algorithm, device, or other means 54 sets weighting factors for the signals applied to the coil segments 38 to induce a current of different amplitude in each coil segment 38 to generate optimally shifted electro-magnetic fields. The RF excitation is performed with a circular excitation polarization. The radio frequency excitation pulses excite magnetic resonance signals in the imaging subject 16 that are spatially encoded by the selected magnetic field gradients. Still further, the imaging controller 48 operates radio frequency receiver or receivers 56 that each is individually controlled and connected with an individual or group of coil sediments 38 of the coil system 34 to demodulate the generated and spatially encoded magnetic resonance signals. The magnetic resonance signals are acquired at a circular receive polarisation that is opposite the excitation polarisation. The received spatially encoded magnetic resonance data is stored in a magnetic resonance or MR data memory 60.

From Maxwell's equations, the following equation containing a complex permittivity can be derived:

$$\nabla \times \underline{\vec{H}}(\vec{r}) = i\omega\underline{\epsilon}(\vec{r})\underline{\vec{E}}(\vec{r}) \tag{1}$$

where $\underline{H}$ is the magnetic field strength,
$\underline{E}$ is the electric field,
r represents coordinates in a field of view,
ω is the Lannor frequency, and
$\underline{\epsilon}$ is the complex permittivity of the electric field.

Equation (1) can be solved for the unknown permittivity $\underline{\epsilon}$ by looking at a z-component:

$$(\partial_x\underline{H}_y(\vec{r}) - \partial_y\underline{H}_x(\vec{r}))/\underline{E}_z(\vec{r}) = i\omega\underline{\epsilon}(\vec{r}) \tag{2}$$

where $H_x$ represents total magnetic field of an x-component generated by N coil elements,
$H_y$ represents total magnetic field of a y-component generated by N coil elements,
$E_z$ represents total electric field of the z-component generated by N coil elements,
ω is the Larmor frequency,
r represents coordinates in the field of view, and
$\underline{\epsilon}$ is the permittivity of the electric field.

From Maxwell's extension of the Ampere law, $$\nabla \times \vec{H}(\vec{r},t) = \vec{j} + \partial_t\vec{D}(\vec{r},t) \tag{3}$$

where j denotes the current density, and
D denotes the electric displacement field.

The electric displacement field D is:

$$\vec{D} = \epsilon\vec{E}$$

and the current density is:

$$\vec{j} = \sigma\vec{E}$$

where ϵ is the permittivity of the electric field and
σ is the conductivity of the electric field.

Assuming the permittivity ϵ being constant in time, Equation (3) can be rewritten as:

$$\nabla \times \vec{H}(\vec{r},t) = \sigma(\vec{r})\vec{E}(\vec{r},t) + \epsilon(\vec{r})\partial_t\vec{E}(\vec{r},t) \tag{4}$$

If $\vec{E}(\vec{r},t) =: \vec{E}'(\vec{r})\exp(i\omega t)$, $\tag{5}$

Equation (4) can be written as Equation (1):

$$\nabla \times \underline{\vec{H}}(\vec{r}) = (\sigma(\vec{r}) + i\omega\epsilon(\vec{r}))\underline{\vec{E}}(\vec{r}) = i\omega\underline{\epsilon}(\vec{r})\underline{\vec{E}}(\vec{r}) \tag{6}$$

The complex permittivity is:

$$\underline{\epsilon}(\vec{r}) = \epsilon(\vec{r}) - i\sigma(\vec{r})/\omega \tag{7}$$

where ϵ is the complex permittivity of the electric field,
$\underline{\sigma}$ is the conductivity of the electric field,
ω is the Larmor frequency, and
r represents coordinates in the field of view.

The real and imaginary parts of the right hand side of Equation (7) are sometimes called "eddy current" and "displacement current", respectively.

If the excitation coil 30 or 36 includes N coil elements 38 which each generates a magnetic field $H^n$ and an electric field $E^n$ (n=1, ... N), Equation (2) becomes:

$$(\partial_x\underline{H}_y^{tot}(\vec{r}) - \partial_y\underline{H}_x^{tot}(\vec{r}))/\underline{\vec{E}}_z^{tot}(\vec{r}) = i\omega\underline{\epsilon}(\vec{r}) \tag{8}$$

where $H_x^{tot}$ represents total magnetic field of an x-component generated by N coil elements,
$H_y^{tot}$ represents total magnetic field of a y-component generated by N coil elements,
$E_z^{tot}$ represents total electric field of the z-component generated by N coil elements,
ω is the Larmor frequency,
r represents coordinates in the field of view, and
$\underline{\epsilon}$ is the permittivity of the electric field.

Equation (8) demonstrates that the permittivity of the electric field is proportional to the inverse z-component of the electric field:

$$\underline{\epsilon} \sim \underline{E}_z^{-1} \tag{9}$$

Thus, the complex permittivity $\underline{\epsilon}$ cannot be accurately determined for regions in which the z-component of the electric field is negligible, i.e. $\underline{E}_z \approx 0$.

Amplitude $A^n$ and phase $\Phi^n$ of each transmit coil element 38 can be adjusted individually. The total electric field $\underline{E}^{tot}$ is:

$$\vec{\underline{E}}^{tot}(\vec{r}) = \sum_{n \leq N} \underline{A}^n \vec{\underline{E}}^n(\vec{r}), \quad (10)$$

where $A^n$ represents amplitude or weight given to each signal,
$E^n$ represents electric field generated by each coil element,
$E^{tot}$ represents total electric field generated by N coil elements, and
r represents coordinates in the field of view.

The z-component of the total electric field is:

$$\underline{E}_z^{tot}(\vec{r}) = \sum_{n \leq N} \underline{A}^n \underline{E}_z^n(\vec{r}), \quad (11)$$

where $A^n$ represents amplitude or weight given to each signal,
$E_z^n$ represents the z-component of the electric field generated by each coil elements,
$E_z^{tot}$ represents total electric field of the z-component generated by N coil elements, and
r represents coordinates in the field of view.

Discretizing the spatial coordinate in a field of view (FOV) with M pixel, Equation (11) can be rewritten as a matrix-vector equation:

$$\underline{E}_z^{tot} = \underline{E}_z \underline{A} \quad (12)$$

where $\underline{E}_z^{tot}$ is a vector containing the M spatial values of $\underline{E}_z^{tot}(\vec{r}_m)$,
$\underline{A}$ is a vector containing the N weighting factors $\underline{A}^n$, and
$\underline{E}_z$ is a matrix containing the M spatial values of the N electric fields $\underline{E}_z^n(\vec{r}_m)$.

With continuing reference to FIG. 1, the weighting processor 54 sets different weighting coefficients or factors $\underline{A}$. An image processor 62 includes an E, H processor 64 which calculates electric field strength E and magnetic induction H for each pixel of an imaged field of view. The electric fields of the different measurements might have zero regions. However, the weighting processor 54 shifts the weighting coefficients sufficiently that the spatial locations of the zero regions of the resulting electric fields differ. Thus, for each spatial location $\vec{r}$ of the FOV, there is at least one measurement where the electric field is significantly different from zero, i.e. $\underline{E}_z^{tot}(\vec{r}) \neq 0$.

Magnetic $B_1$ field is influenced by the weighting coefficients $\underline{A}$. To ensure a sufficient spin excitation, the relevant, circularly polarized component of the magnetic $B_1$ field has to be large enough.

Figure 2:
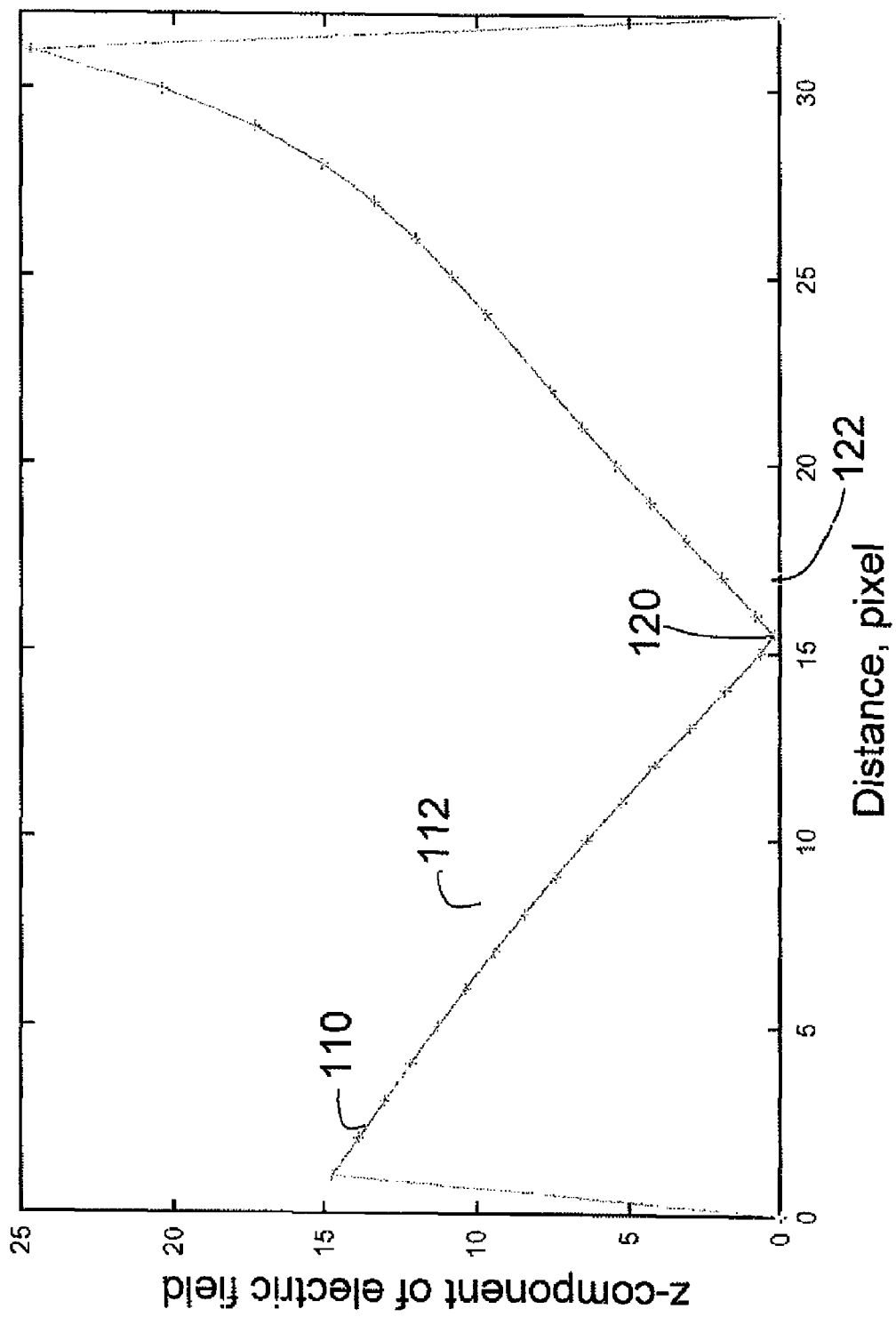
FIG. 2 illustrates shifted profiles of the electric fields.

With reference to FIG. 2, two shifted profiles 110, 112 of the total electric field $\vec{\underline{E}}_z^{tot}(\vec{r})$ of the z-component are shown. Varying the weighting coefficients $\underline{A}^n$ shifts a zero point 120 of the profile 110 a couple of pixels to a zero point 122 of the profile 112.

With reference again to FIG. 1, the calculated values of the electric field strength E and magnetic induction H for each pixel of an imaged field of view are stored in corresponding E and H memories 130, 132. An electric permittivity map computing device, processor, algorithm, or other means 140 eliminates zero values of the total electric field by superpositioning the generated shifted electric fields and computes an electric permittivity or $\epsilon$ map or distribution 142. The electric permittivity $\epsilon$ can be accurately determined for the entire field of view.

Figure 3:
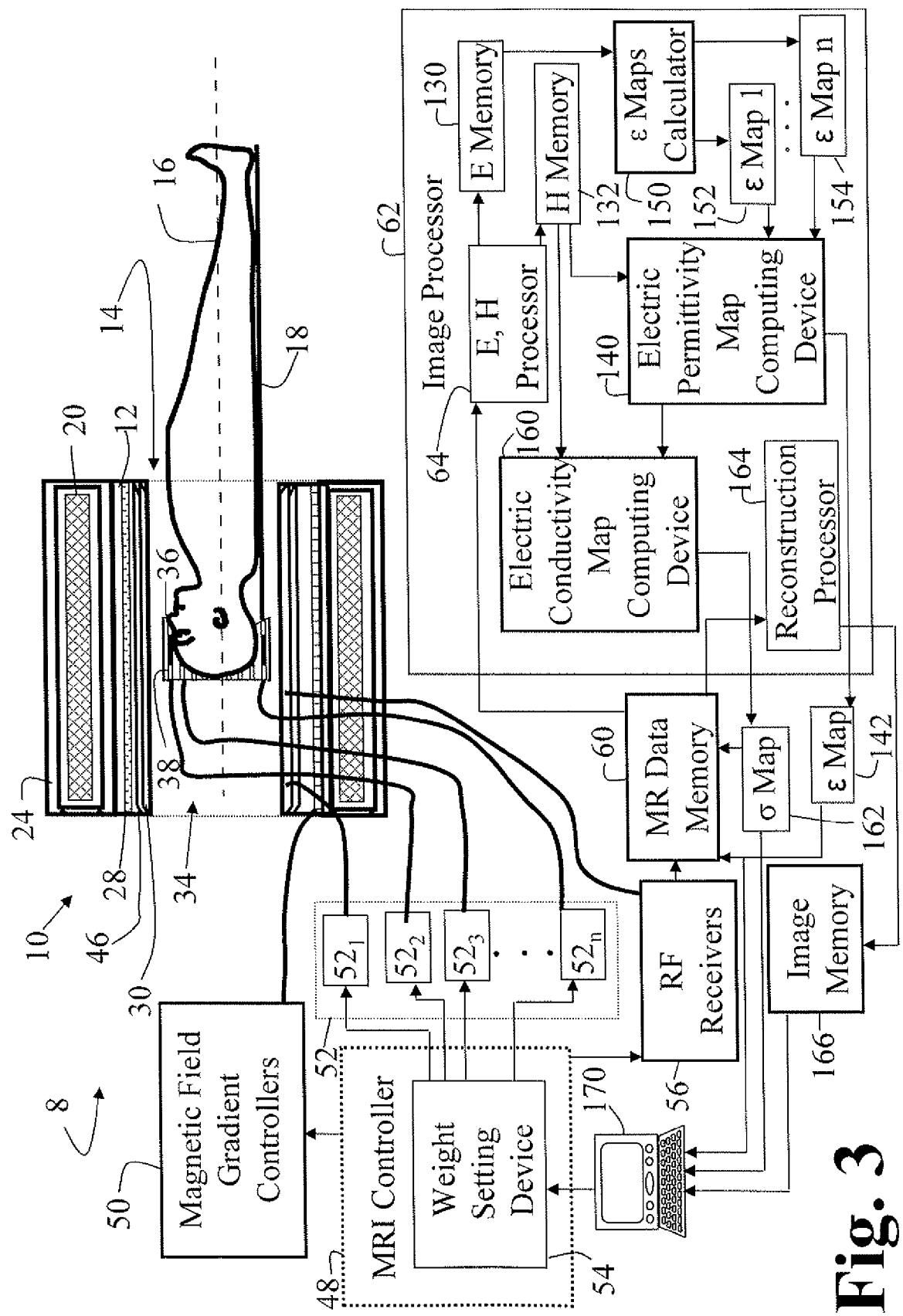
FIG. 3 is a diagrammatic illustration of another embodiment of a magnetic resonance system.

With reference to FIG. 3, in this embodiment, an electric permittivity or $\epsilon$ maps calculator 150 calculates two or more shifted permittivity maps 152, 154 from the electric field and magnetic induction maps with differently set weighting coefficients. The electric permittivity map computing device 140 computes the electric permittivity map or distribution 142 from a combination of the shifted permittivity maps 152, 154. Thus, in this example, between the two different permittivity maps, the electric permittivity $\epsilon$ can be determined for the entire field of view. Of course, more than two shifted permittivity maps can be generated.

Of course, it is contemplated that the desired electric field $\underline{E}_z^{tot}$ is chosen as $\underline{E}_0(r) \approx$ constant over the entire field of view. However, for a birdcage coil, this is only possible at a trade off of choosing constant to be very small.

In this manner, for every pixel in the field of view, one of the coil elements generates the electric field with a z-component value unequal to zero. Permittivity values should be consistent in all maps for the shifted pixels at which $E_z$ approaches zero. In a two maps embodiment, when the permittivity value of corresponding pixels is different, particularly when the value in one map is much higher than neighboring values, the lower value can be selected as the true value for the pixel. In other embodiments, where a larger number of permittivity maps with differently shifted electric fields are generated, the permittivity value for each pixel can be based on an averaging or combining of the values for each pixel that match within a selected deviation. Various other techniques for choosing the values for each pixel are also contemplated.

A further optimization of the electric fields (yielding a stronger separation of the zero regions) is expected by further evaluation of suitable desired $\vec{\underline{E}}_z^{tot}(\vec{r})$. In the presented example, a linear desired $\vec{\underline{E}}_z^{tot}(\vec{r}) \sim |\vec{r} - \vec{r}_0|$ is chosen for simplicity.

The spatial transmit sensitivity distribution of an RF coil is given by the H component circularly polarized in one direction, which might be defined as the "positive" direction. If the static magnetic field has a negative z-direction, the transmit component is:

$$\underline{H}^+ = (\underline{H}_x + i\underline{H}_y)/2 \quad (13)$$

The spatial receive sensitivity distribution of an RF coil is given by the H component circularly polarized in the opposite direction than in the transmit case, i.e. the "negative" direction:

$$\underline{H}^- = (\underline{H}_x - i\underline{H}_y)/2 \quad (14)$$

Thus, the components $\underline{H}_x$ and $\underline{H}_y$ can be deduced from Equations (13)-(14).

The transmit and receive sensitivities can be determined as:

$$\underline{S}(\vec{r}) \approx \underline{M}_0(\vec{r}) \underline{H}^-(\vec{r}) \sin(k \underline{H}^+(\vec{r})) \quad (15)$$

where S is the image signal intensity, and
k is a system dependent constant.

With reference again to FIG. 1 and continuing reference to FIG. 3, an electric conductivity map computing device, processor, algorithm, or other means 160 computes electric conductivity distribution or σ map 162 in the imaged subject from the magnetic field strength distribution.

A reconstruction processor, algorithm, device, or other means 164 reconstructs the magnetic resonance data into a reconstructed image of the imaging subject 16 or a selected portion thereof lying within the examination region 14. The reconstruction processor 164 also reconstructs volumetric datasets or tomographic cross sectional images from the electrical permittivity distribution. The reconstruction processor 164 employs a Fourier transform reconstruction technique or other suitable reconstruction technique that comports with the spatial encoding used in the data acquisition. The reconstructed image is stored in an image memory 166, and can be displayed on a user interface 170, transmitted over a local area network or the Internet, printed by a printer, or otherwise utilized. In the illustrated embodiment, the user interface 170 also enables a radiologist or other user to interface with the imaging controller 48 to select, modify, or execute imaging sequences. In other embodiments, separate user interfaces are provided for operating the scanner 10 and for displaying or otherwise manipulating the reconstructed images. The permittivity and/or conductivity maps 142, 162 can also be displayed on the user interface 170, transmitted over a local area network or the Internet, printed by a printer, or otherwise utilized.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging apparatus comprising:
    a radio frequency coil system for generating radio frequency excitation pulses in an examination region, radio frequency coil system including N coil elements which generate magnetic and electric fields, where N is a plural number;
    a weight setting device which sets weight factors for input signals for the coil elements;
    a transmitting system, which creates RF pulses, at least two sets of each with differently weighted input signals, and transmits the at least two sets of RF pulses to the coil elements such that each of the transmitted RF pulse sets generates shifted electric fields having a shifted zero crossing point from each other; and
    an image processor which computes electric permittivity (ϵ) maps from resonance induced by the at least two sets of RF pulses with different weighting, the image processor including:
        a memory arrangement which holds the ϵ maps generated with the RF pulse sets;
        an algorithm or processor which combines the ϵ maps from the at least two RF pulse sets to generate a corrected ϵ map corrected for regions in which the electric fields is near zero in one of the ϵ maps.

2. The apparatus as set forth in claim 1, wherein the image processor includes:
    an electric conductivity map computing processor which computes electric conductivity distribution in the imaged subject.

3. The apparatus as set forth in claim 1, wherein the electric permittivity ϵ is proportional to an inverse z-component of a computed total electric field having values unequal to zeroes so that the electric permittivity distribution of an entire field of view is computed:

$$(\partial_x \underline{H}_y^{tot}(\vec{r}) - \partial_y \underline{H}_x^{tot}(\vec{r}))/\vec{E}_z^{tot}(\vec{r}) = i\omega\underline{\epsilon}(\vec{r})$$

where $\underline{H}_x^{tot}$ represents total magnetic field of an x-component generated by N coil elements,
$\underline{H}_y^{tot}$ represents total magnetic field of a y-component generated by N coil elements,
$E_z^{tot}$ represents total electric field of the z-component generated by N coil elements,
ω is the Larmor frequency,
r represents coordinates in the field of view, and
$\underline{\epsilon}$ is the permittivity of the electric field.

4. The apparatus as set forth in claim 3, wherein the total electric field of the z-component is.

$$\underline{E}_z^{tot}(\vec{r}) = \sum_{n \leq N} \underline{A}^n \underline{E}_z^n(\vec{r})$$

where $\underline{A}^n$ represents weight factors for the coil elements,
$\underline{E}_z^{tot}$ tot represents total electric field of the z-component generated by N coil elements,
$\underline{E}_z^n$ represents electric fields of the coil elements, and
r represents coordinates in the field of view.

5. The apparatus as set forth in claim 1, wherein the image processor includes:
    an electric permittivity map computing device which superpositions shifted electric fields to receive non-zero values of a total electric field and computes an electric permittivity map from the superpositioned data.

6. The apparatus as set forth in claim 1, wherein each element of the coil system is driven independently via a channel of the transmitting system to selectively apply RF pulses to the examination region to generate a circularly polarized magnetic induction field which has an excitation polarization orientation.

7. The apparatus as set forth in claim 6, wherein each element of the coil system is an independent receiving element, which is connected to a channel of a receiver to demodulate received MR signals of the circularly polarized magnetic induction field with a reception polarization orientation.

8. The apparatus as set forth in claim 1, wherein the coil system includes an RF coil which includes a plurality of resonators (38) extending parallel to a main magnetic fields.

9. A method for determining at least one electromagnetic property of a subject, the method comprising:
    a) setting a weight factor for an input signal for each individual radio frequency coil element;
    b) transmitting RF pulses with the set weight factors to corresponding coil elements to generate a first set of resonance data in which an electric field approaches zero at least one zero electric field point;
    c) repeating steps (a) and (b) with different weighting factors to generate at least a second of resonance data with at least one zero electric field point, the zero electric field points of the first and second sets of resonance data being spatially shifted; and
    d) reconstructing an electric permittivity map from the first and second sets of resonance data without using resonance data at or adjacent the zero electric field points in either of the first and second sets of resonance data.

10. The method as set forth in claim 9, wherein the step (d) includes:
    superpositioning the shifted electric fields;

computing z-component values of a total electric field strength distribution which values are unequal to zeroes; and computing electric permittivity distribution in the subject from the superpositioned data.

11. The method as set forth in claim 9, wherein the electric permittivity is proportional to an inverse z-component of the electric field.

12. The method as set forth in claim 9, further including:

independently driving each coil element via a channel of the transmitting system;

selectively applying RF pulses to the examination region; and generating a circular polarized magnetic induction field which has an excitation polarization orientation.

13. The method as set forth in claim 12, further including:

receiving MR signals of the circular polarized magnetic induction field with plurality of independent receiving elements in a reception polarisation orientation; and demodulating the received MR signals.

14. The method as set forth in claim 9, wherein the coil system includes an RF coil which includes a plurality of resonators extending parallel to a main magnetic field.

15. The method as set forth in claim 9, further including:

computing electric conductivity distribution in the imaged subject.

16. The method as set forth in claim 9, further including:

reconstructing a volumetric data image representation from the electric permittivity distribution.

17. A magnetic resonance imaging system for performing the steps of claim 9.

18. A system for deriving electromagnetic properties of an imaged subject, the system comprising:

a main magnet which generates a main magnetic field through an examination region;

a plurality of RF coil elements disposed adjacent the examination region for generating magnetic and electric fields;

a weight setting device which sets weight factors for input signals for the coil elements;

a transmitting system, which creates RF pulses in accordance with the determined input signals and transmits the RU pulses to corresponding coil elements such that the transmitted RF pulses generate first electric fields having a zero electrical field point and second electrical field having a zero electrical filed point, a z-component value of the first and second generated electric fields having shifted zero electrical filed points;

an electric permittivity map computing processor which combines the shifted first and second generated electric fields to create a total electric field without a zero crossing point and computes electric permittivity distribution in the imaged subject based on the total electric filed; and a reconstruction processor which reconstructs a volumetric data representation of an entire field of view from the computed electric permittivity distribution.

19. The system as set forth in claim 18, wherein the electric permittivity is proportional to an inverse z-component of the total electric field:

$$(\partial_x \underline{H}_y^{tot}(\vec{r}) - \partial_y \underline{H}_x^{tot}(\vec{r}))/\vec{E}_z^{tot}(\vec{r}) = i\omega\underline{\epsilon}(\vec{r})$$

where $\underline{H}_x^{tot}$ represents total magnetic field of an x-component generated by N coil elements, where $\underline{H}_y^{tot}$ represents total magnetic field of a y-component generated by N coil elements, $E_z^{tot}$ represents total electric field of the z-component generated by N coil elements, $\omega$ is the Larmor frequency, r represents coordinates in the field of view, and $\underline{\epsilon}$ is the permittivity of the electric field.

* * * * *